(12) United States Patent
Bender et al.

(10) Patent No.: US 7,767,856 B2
(45) Date of Patent: *Aug. 3, 2010

(54) SYSTEM AND METHOD FOR PRODUCING ARYLAMINE COMPOUNDS

(75) Inventors: Timothy P. Bender, Toronto (CA); Emily L. Moore, Mississauga (CA); Jennifer A. Coggan, Cambridge (CA); Frank Ping-Hay Lee, Oakville (CA); David Borbely, Simcoe (CA)

(73) Assignee: Xerox Corporation, Norwalk, CT (US)

( * ) Notice: Subject to any disclaimer, the term of this patent is extended or adjusted under 35 U.S.C. 154(b) by 47 days.

This patent is subject to a terminal disclaimer.

(21) Appl. No.: 11/698,314

(22) Filed: Jan. 25, 2007

(65) Prior Publication Data

US 2008/0183017 A1    Jul. 31, 2008

(51) Int. Cl.
  *C07C 209/00* (2006.01)
(52) U.S. Cl. .................. 564/405; 564/406; 564/407; 564/433; 564/305; 564/307
(58) Field of Classification Search ......... 564/405–407, 564/433, 305, 307
See application file for complete search history.

(56) References Cited

U.S. PATENT DOCUMENTS

| | | | |
|---|---|---|---|
| 4,265,990 A | 5/1981 | Stolka et al. | |
| 5,709,974 A | 1/1998 | Yuh et al. | |
| 5,891,594 A | 4/1999 | Yuh et al. | |
| 6,100,398 A * | 8/2000 | Hartwig et al. | ............. 544/264 |
| 2006/0111588 A1 | 5/2006 | Bender | |

FOREIGN PATENT DOCUMENTS

EP    1 676 632 A1    7/2006

OTHER PUBLICATIONS

U.S. Appl. No. 11/274,506, filed Nov. 16, 2005, Coggan et al.
U.S. Appl. No. 11/263,671, filed Nov. 1, 2005, Coggan et al.
U.S. Appl. No. 10/992,690, filed Mar. 6, 2003, Bender et al.
Journal of Organometallic Chemistry, "Successful application of microstructured continuous reactor in the palladium catalysed aromatic amination," C. Mauger et al., 690, (2005), pp. 3627-3629.
European Search Report, Application No. EP 08 10 0688, dated Apr. 24, 2008, 6 pages.

\* cited by examiner

*Primary Examiner*—Karl J Puttlitz
*Assistant Examiner*—Sudhakar Katakam
(74) *Attorney, Agent, or Firm*—Pillsbury Winthrop Shaw Pittman LLP

(57) ABSTRACT

Improved methods for making hole transport molecules (HTMs) that are incorporated into imaging members, such as layered photoreceptor devices, to increase the photoreceptor's "hole mobility," or its ability to move charge, across its charge transport layer (CTL). Embodiments pertain to a continuous process for making N,N-diphenyl-4-biphenylamine and a system for performing the same.

6 Claims, 3 Drawing Sheets

SYSTEM AND METHOD FOR PRODUCING ARYLAMINE COMPOUNDS

TECHNICAL FIELD

The present disclosure relates generally to improved methods and processes for making hole transport molecules (HTMs) that are incorporated into imaging members, such as layered photoreceptor devices, to increase the photoreceptor's "hole mobility," or its ability to move charge, across its charge transport layer (CTL). The imaging members can be used in electrophotographic, electrostatographic, xerographic and like devices, including printers, copiers, scanners, facsimiles, and including digital, image-on-image, and like devices. More particularly, the embodiments pertain to a continuous method for making N,N-diphenyl-4-biphenylamine that uses a continuous plug flow reactor for performing the same.

BACKGROUND

In electrophotography, also known as xerography, electrophotographic imaging or electrostatographic imaging, the surface of an electrophotographic plate, drum, belt or the like (imaging member or photoreceptor) containing a photoconductive insulating layer on a conductive layer is first uniformly electrostatically charged. The imaging member is then exposed to a pattern of activating electromagnetic radiation, such as light. Charge generated by the photoactive pigment moves under the force of the applied field. The movement of the charge through the photoreceptor selectively dissipates the charge on the illuminated areas of the photoconductive insulating layer while leaving behind an electrostatic latent image. This electrostatic latent image may then be developed to form a visible image by depositing oppositely charged particles on the surface of the photoconductive insulating layer. The resulting visible image may then be transferred from the imaging member directly or indirectly (such as by a transfer or other member) to a print substrate, such as transparency or paper. The imaging process may be repeated many times with reusable imaging members.

An electrophotographic imaging member may take one of many different forms. For example, layered photoresponsive imaging members are known in the art. U.S. Pat. No. 4,265,990, which is incorporated herein by reference in its entirety, describes a layered photoreceptor having separate photogenerating and charge transport layers. The photogenerating layer is capable of photogenerating holes and injecting the photogenerated holes into the charge transport layer. Thus, in photoreceptors of this type, the photogenerating material generates electrons and holes when subjected to light.

More advanced photoconductive receptors contain highly specialized component layers. For example, a multilayered photoreceptor that can be employed in electrophotographic imaging systems can include one or more of a substrate, an undercoating layer, an optional hole or charge blocking layer, a charge generating layer (including photogenerating material in a binder, e.g., photoactive pigment) over the undercoating and/or blocking layer, and a charge transport layer (including charge transport material in a binder). Additional layers such as an overcoating layer or layers can also be included. See, for example, U.S. Pat. Nos. 5,891,594 and 5,709,974, which are incorporated herein by reference in their entirety.

The photogenerating layer utilized in multilayered photoreceptors can include, for example, inorganic photoconductive particles or organic photoconductive particles dispersed in a film forming polymeric binder. Inorganic or organic photoconductive material may be formed as a continuous, homogeneous photogenerating layer.

Upon exposure to light, the charge generated is moved through the photoreceptor. The charge movement is facilitated by the charge transport layer. The speed with which the charge is moved through the charge transport layer directly affects how fast the machine can operate. To achieve the desired increase in machine speed (ppm), the ability of the photoreceptor to move charge must also be increased. Thus, enhancement of charge transport across these layers provides better photoreceptor performance.

Conventional hole transport molecules, such as for example N,N'-diphenyl-N,N-bis(3-methylphenyl)-1,1'-biphenyl-4,4'-diamine, are generally incorporated into the charge transport layer to help mobility. However, as electrophotography advances, there is a growing need to further improve machine speed and devise ways to make different arylamine compounds that can be used to improve the hole mobility of existing photoreceptors. There has been historically very few synthesis reactions to produce variations in the arylamine structure. The Ullmann and Goldberg reactions have been generally used to produce triarylamines or diarylamines. These reactions, however, use large amounts (e.g., up to 10 mol equivalents) of solid, insoluble hydroxide or carbonate bases and thus are heterogeneous. The heterogeneity prevents these reactions from being conducted in a continuous mode to yield a higher and purer amount of product.

Recently, Buchwald chemistry has been used in place of the conventional Ullmann chemistry to produce arylamines not previously accessible. Buchwald chemistry has distinct benefits over the previously used methods in that the process cycle time is less, energy consumption is less and the crude product purity is higher, as disclosed generally in U.S. Patent Application Publication No. 2006/0111588 and U.S. patent application Ser. No. 10/992,690 to Bender et al., filed Mar. 6, 2003, which are hereby incorporated by reference. Other more specific methods involving Buchwald Chemistry are disclosed in U.S. patent application Ser. No. 11/263,671 to Coggan et al., filed Nov. 1, 2005, and Ser. No. 11/274,506 to Coggan et al., filed Nov. 16, 2005, which are hereby incorporated by reference. Thus, Buchwald chemistry has been found to be more advantageous to use over the traditional methods and processes.

One issue that has been faced with using Buchwald chemistry, however, is that highly exothermic processes are involved in the production of the arylamine compounds. While these exothermic reactions do not present a problem when performed on a smaller scale, the reactions can present a safety risk when used in large-scale productions in batch mode due to the increase in reactant volume to heat transfer area ratio which makes heat management more difficult. A continuous mode production using Buchwald chemistry would avoid such safety risks and allow optimal conversion to product on a large-scale by increasing the heat transfer area available to the reacting volume. Unfortunately, Buchwald chemistry also produces a precipitate during the reaction, resulting in a heterogeneous mixture, which precludes performing Buchwald reactions in a continuous mode due to plugging/fouling of the reactor by the precipitate.

Thus, it is desirable to devise a new method in which continuous manufacture of arylamines can be performed using Buchwald reactions, even on a large-scale production.

The term "electrostatographic" is generally used interchangeably with the term "electrophotographic." In addition, the terms "charge blocking layer" and "blocking layer" are generally used interchangeably with the terms "undercoat layer." In addition, the term "arylhalide" is generally used interchangeably with the terms "haloaryl" and "haloaromatic."

BRIEF SUMMARY

According to embodiments illustrated herein, there is provided an improved method using Buchwald chemistry that maintains a homogeneous mixture throughout the process so that the method can be performed continuously, and an apparatus for performing the same that addresses the needs discussed above.

An embodiment may include a method for forming an arylamine, comprising reacting an amine compound with an arylhalide compound in a presence of a base and a ligated palladium catalyst in a continuous plug flow reactor such that an arylamine compound is produced, wherein all products and by-products remain solubilized.

In another embodiment, there is provided a method for forming an arylamine, comprising adding 4-bromobiphenyl and diphenylamine in toluene into a continuous plug flow reactor, the continuous plug flow reactor further comprising continuously reacting the 4-bromobiphenyl and the diphenylamine in the toluene in a presence of a base and a palladium catalyst under Buchwald conditions in the continuous plug flow reactor, adding a phosphonium-based ionic liquid with tri-t-butylphospine to the 4-bromobiphenyl and the diphenylamine in the continuous plug flow reactor, continuously reacting the 4-bromobiphenyl and the diphenylamine in the toluene and the phosphonium-based ionic liquid with the tri-t-butylphospine in the presence of the base and the palladium catalyst under Buchwald conditions in the continuous plug flow reactor until N,N-diphenyl-4-biphenylamine is produced, and collecting the N,N-diphenyl-4-biphenylamine.

Another embodiment may include a system for forming an arylamine, comprising one or more reagents for forming an arylamine, a palladium catalyst for initiating the formation of the arylamine, a continuous plug flow reactor for receiving the one or more reagents and the palladium catalyst, the continuous plug flow reactor further comprising one or more input pots for receiving one or more reagents, one or more compressed air or nitrogen inlets coupled to the one or more input pots for introducing compressed air or nitrogen into the one or more reagents, a tubular reactor suspended in an immersion bath and in flow communication with the one or more input pots for continuously reacting the one or more reagents, and a circulation heating and refrigeration bath unit in flow communication with the immersion bath for controlling a temperature of the one or more reagents inside the tubular reactor, and a product receiver unit adapted to collect and weigh the arylamine produced.

BRIEF DESCRIPTION OF THE DRAWINGS

For a better understanding of the present embodiments, reference may be had to the accompanying figures.

DETAILED DESCRIPTION

Figure 1:
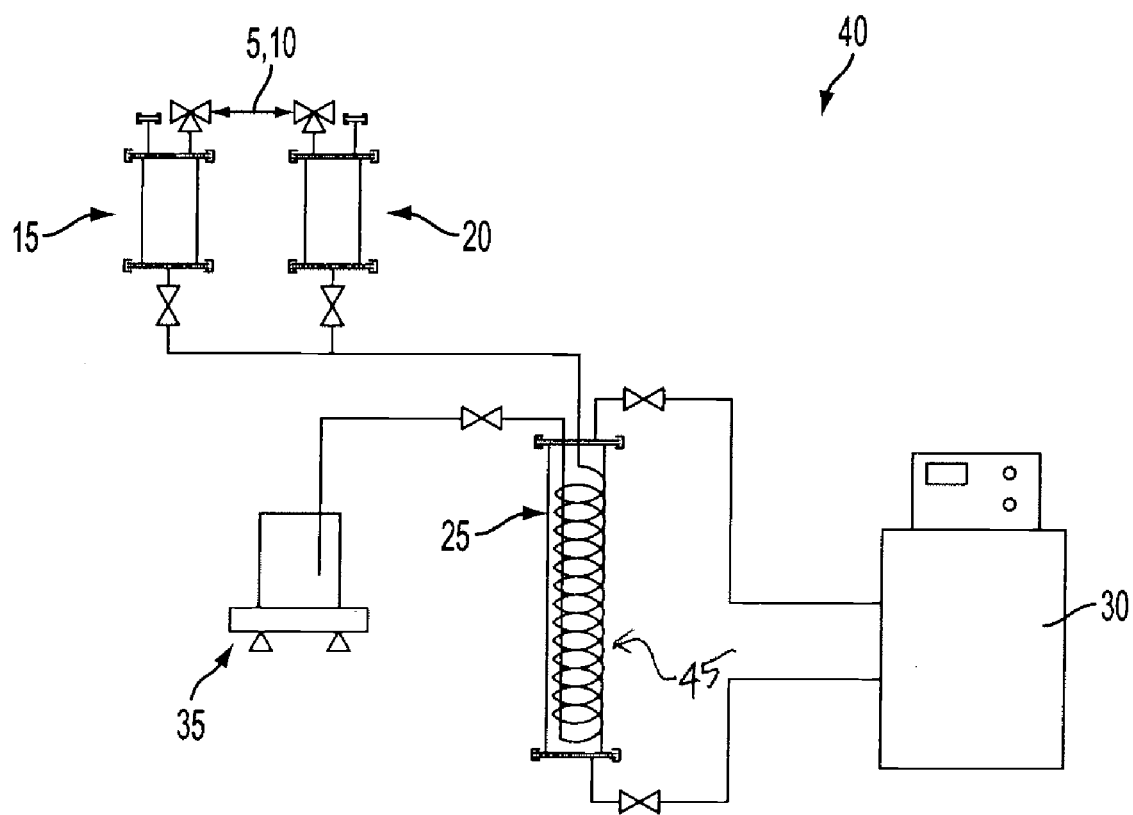
FIG. 1 is a schematic diagram of an embodiment of a system according to an embodiment of the present disclosure.

It is understood that other embodiments may be utilized and structural and operational changes may be made without departure from the scope of the embodiments disclosed herein.

The present embodiments relate to novel methods useful for making hole transport molecules (HTMs) that are incorporated into imaging members, such as layered photoreceptor devices. These molecules, asymmetric or symmetric arylamine compounds, are used to increase the photoreceptor's hole mobility across its charge transport layer (CTL). Improved chemical methods for making these arylamines comprise synthesis using a Buchwald reaction sequence that maintains homogeneity of product and can thus be performed continuously. The embodiments also relate to an apparatus for performing the Buchwald reaction in a continuous mode.

In embodiments, the apparatus is a continuous plug flow reactor (PFR). A continuous plug flow reactor is essentially a type of vessel designed to contain chemical reactions. The plug flow reactor model is used to estimate the key unit operation variables when using a continuous tubular reactor to reach a specified output. In a plug flow reactor, the fluid passes through in a coherent manner, so that the residence time, $\tau$, is the same for all fluid elements. The coherent fluid passing through the ideal reactor is known as a plug. The plug flow reactors are used to model the chemical transformation of compounds as they are transported in systems with a variety of conduits through which the liquids or gases flow, in the present embodiments, pipelines.

As discussed briefly above, performing Buchwald reactions in continuous mode is desirable over batch mode due to safety concerns. Because Buchwald chemistry can be a highly exothermic process for certain combinations of reagents and substrates, using such chemistry on a large scale may involve safety risks. A continuous mode process minimizes this risk by increasing significantly the heat transfer area to the reaction volume ratio and heat transfer rate. In addition, using a continuous mode provides several advantages over the traditional methods and processes of making arylamines. For example, if a reaction begins to hit a runaway point, the heat can be reduced or turned off and due to the great heat transferability, reagents can be cooled faster. The improved temperature control also makes it easier to find and maintain an optimal temperature that will achieve high product conversion. In this manner, high conversion may be achieved at lower temperatures. By leaving a continuous process on for a longer period of time translates into being able to produce larger amounts of material, while still ensuring that only a small portion of the material is at reaction temperature at any one time. Thus, larger scale production of the arylamines can be achieved without safety risks.

The arylamine compound or molecule produced by the present embodiments are used to serve as a hole transport molecule. The embodiments include an improved method for making arylamines using a continuous Buchwald reaction to achieve the formation of carbon-nitrogen bonds. Buchwald chemistry recognizes the general versatility of palladium-based catalysts for the formation of these bonds. The present disclosure adapts the procedure for the continuous production of various arylamine compounds, including but not limited to monomeric, dimeric, and trimeric arylamine compounds. The present embodiments comprise a general Buchwald reaction of an arylhalide with an arylamine in the presence of a compatible solvent to produce an arylamide compound. In further embodiments, the present embodiments comprise a Buchwald reaction of an arylhalide compound with an amine compound in the presence of a base and a ligated palladium catalyst to produce an arylamine where all products and by-products remain solubilized. In embodiments, the reaction is conducted in a continuous plug flow reactor.

According to embodiments, an arylhalide such as an arylbromide and an arylamine are used as starting materials. Any suitable arylhalide can be used, such as arylbromides, arylchlorides, aryliodides, arylfluorides, and the like. Likewise, any suitable arylamine can be used. The selection of specific starting arylhalide and arylamine depend, for example, upon the desired final product. For example, in embodiments, the arylamine is an arylbromide such as 4-bromobiphenyl and the arylamine is diphenylamine, which react to form the arylamine N,N-diphenyl-4-aminobiphenyl.

In embodiments, where an arylbromide is used, the reaction, including the starting materials and final product, can generally be represented as follows:

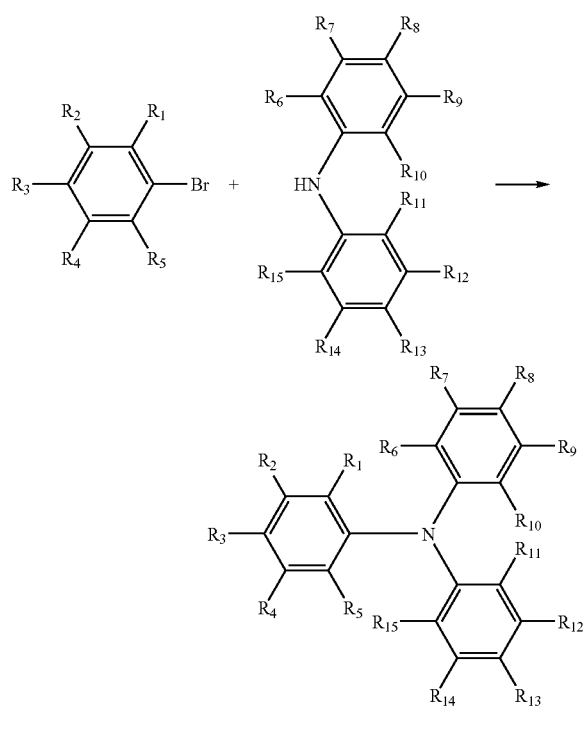

In this reaction scheme, the arylbromide can be any suitable arylbromide, depending upon the desired final product. Thus, for example, in the above reaction scheme, the substituents $R^1$, $R^2$, $R^3$, $R^4$ and $R^5$, which can be the same or different, can be suitably selected to represent hydrogen, a halogen, an alkyl group having for example from 1 to about 20 carbon atoms (such as methyl, ethyl, propyl, butyl and the like), a hydrocarbon radical having for example from 1 to about 20 carbon atoms, an aryl group optionally substituted by one or more alkyl groups, an alkyl group containing a heteroatom such as oxygen, nitrogen, sulfur and the like having for example from 1 to about 20 carbon atoms, a hydrocarbon radical containing a heteroatom such as oxygen, nitrogen, sulfur and the like having for example from 1 to about 20 carbon atoms, an aryl group containing a heteroatom such as oxygen, nitrogen, sulfur and the like optionally substituted by one or more alkyl groups, and the like. In embodiments, one of $R^1$, $R^2$, $R^3$, $R^4$ and $R^5$, such as $R^3$, represents a phenyl group and the remaining represent H atoms. Thus, in this embodiment, the arylbromide is 4-bromobiphenyl.

Likewise, in this reaction scheme, the arylamine can be any suitable arylamine, depending upon the desired final product. Thus, for example, in the above reaction scheme, the substituents $R^6$, $R^7$, $R^8$, $R^9$, $R^{10}$, $R^{11}$, $R^{12}$, $R^{13}$, $R^{14}$, and $R^{15}$, which can be the same or different, can be suitably selected to represent hydrogen, a halogen, an alkyl group having for example from 1 to about 20 carbon atoms (such as methyl, ethyl, propyl, butyl and the like), a hydrocarbon radical having for example from 1 to about 20 carbon atoms, an aryl group optionally substituted by one or more alkyl groups, an alkyl group containing a heteroatom such as oxygen, nitrogen, sulfur and the like having for example from 1 to about 20 carbon atoms, a hydrocarbon radical containing a heteroatom such as oxygen, nitrogen, sulfur and the like having for example from 1 to about 20 carbon atoms, an aryl group containing a heteroatom such as oxygen, nitrogen, sulfur and the like optionally substituted by one or more alkyl groups, and the like. In embodiments, each of $R^6$, $R^7$, $R^8$, $R^9$, $R^{10}$, $R^{11}$, $R^{12}$, $R^{13}$, $R^{14}$, and $R^{15}$ represent H atoms. Thus, in certain embodiments, the arylamine is diphenylamine.

The reactants are reacted in the presence of a suitable catalyst. Although not particularly limited, suitable catalysts are those that are known or discovered to be useful for formation of nitrogen-carbon bonds. For example, suitable catalysts include palladium ligated catalysts, such as those disclosed by Buchwald et al. and Hartwig et al. (for example in Michele C. HARRIS et al; "One-Pot Synthesis of Unsymmetrical Triarylamines from Aniline Precursors"; *J. Org. Chem.* Vol. 65, pp. 5327-5333 (2000), the disclosure of which is totally incorporated herein by reference).

In embodiments, a particular suitable catalyst is a palladium acetate ligated with tri-t-butylphosphine or CYTOP-216 and sodium t-butoxide base. The structure of CYTOP-216 organophosphine or 2,4,6-trioxa-1,3,5,7-tetramethyl-8-phosphaadamantane (available from Cytec Industries Inc., West Paterson, N.J.) and tri-t-butylphosphine is shown respectively below:

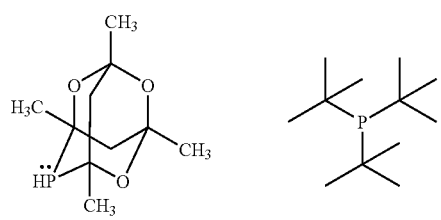

However, it will be apparent that other ligands, such as tri- or di-substituted phosphine ligands, could also be used to produce suitable results (from the point of view of conversion and yield), and thus would be suitable to ligate palladium or other metals and thus act to catalyze the process described in this disclosure. It will also be obvious to those skilled in the art that the use of phosphine-type ligands to ligate palladium may not the only method known or to become know to allow palladium to have catalytic activity under the described conditions. For example, nitrogen, oxygen or other heteroatom containing organic compounds as well as halogens are known to ligate to palladium.

The solvent may be selected from the group consisting of toluene, xylene, pentane, dioxane, ether, hexane, decane, other hydrocarbon solvents (either aromatic or saturated hydrocarbons), other ethers such as tetrahydrofuran, dimethoxyethane, and alcohols such as butanol, hexanol and the like and mixtures thereof. The arylhalide and the arylamine are reacted in the presence of a palladium catalyst. In an embodiment, the catalyst comprises a palladium ligated catalyst.

It was discovered that introducing a co-solvent at a subsequent time to the initial mixture maintained the homogeneity of the overall mixture by preventing the formation of a precipitate. The co-solvent system allows the Buchwald reaction to proceed continuously. In embodiments, the classes of co-solvent used were polyethylene glycol dimethyl ethers and phosphonium-based ionic liquids.

In further embodiments, the co-solvent may be any liquid which could be useful for solubilizing the by-products of the reaction, in particular the inorganic salts that are produced during the reaction. The co-solvents may be selected from the group consisting of linear cown ethers, including any alkylene glycols or glymes such as polyethylene glycol dimethyl ether, and tetraethylene glycol dimethyl ether, cyclic crown ethers, and ionic liquids such as imidizolium based ionic liquids or phosphonium based ionic liquids and mixtures thereof.

The choice of specific solvent, co-solvent or mixture thereof can be decided based on the solubility of the starting materials, intermediates and final products, and will be readily apparent or within routine experimentation to those skilled in the art. Furthermore the choice of solvent, co-solvent or mixture thereof can be decided based on the desired operating temperature range. The reaction should be conducted under an atmosphere of inert gas (such as nitrogen or argon) so as to preclude deactivation of catalyst or base by oxygen or atmospheric moisture.

After the reaction is completed, suitable separation, filtration, and/or purification processes can be conducted, as desired to a desired purity level. For example, the desired arylamine product can be subjected to conventional organic washing steps, can be separated, can be decolorized (if necessary), treated with known absorbents (such as silica, alumina and clays, if necessary) and the like. The final product can be isolated, for example, by a suitable recrystallization procedure. The final product can also be dried, for example, by air drying, vacuum drying, or the like. All of these procedures are conventional and will be apparent to those skilled in the art.

According to embodiments herein, shown in FIG. 1, there is further provided a system that performs the new methods described herein. In particular embodiments, the system uses a continuous plug flow reactor 40 adapted for use in performing the continuous method in which one or more fluid reagents, such as for example, the arylhalide and arylamine, are continuously pumped through a pipe or tube, also known as a "tubular reactor" 25. The reagents are selected based on the desired arylamine compound to produce. The chemical reaction continuously proceeds as the reagents travel through the plug flow reactor 40. Reagents may be introduced into the plug flow reactor 40 at locations in the reactor other than the feed or input pots 15, 20. In this way, a higher efficiency may be obtained, or the size and cost of the plug flow reactor 40 may be reduced. As the plug flow reactor 40 has higher efficiency, given the time-space considerations, the reaction will proceed to a higher percentage of completion than in other types of reactors.

In the system, the reagents or starting materials are added into the continuous plug flow reactor 40 through the input pots 15, 20 from which the materials travel to the tubular reactor 25. Compressed air or nitrogen is let into the plug flow reactor 40 through compressed air or nitrogen inlets 5, 10. The compressed air or nitrogen acts as the driving force for transporting the reagents through the reactor; in an alternate set-up a pump could be used for this purpose. The materials are mixed and reacted continuously in the tubular reactor 25 in the presence of the palladium catalyst and the co-solvent may be added at a subsequent time and location to the reacting materials. The tubular reactor 25 is suspended in an immersion bath 45. A heat transfer medium (such as ethylene glycol) is circulated through the immersion bath 45 from a circulation heating and refrigeration bath unit 30. The circulation heating and refrigeration bath unit 30 is used to maintain a constant temperature around the reactor by providing the necessary heat to start the reaction, then absorbing and removing any heat generated by the reaction. The mixture is passed once through the plug flow reactor 40 as conversion to the product, an arylamine compound, takes place. The subsequent product resulting from the continuous method is collected or recovered by a product receiver 35 which includes a weigh scale to determine the final amount of product recovered.

While the description above refers to particular embodiments, it will be understood that many modifications may be made without departing from the spirit thereof. The accompanying claims are intended to cover such modifications as would fall within the true scope and spirit of embodiments herein.

The presently disclosed embodiments are, therefore, to be considered in all respects as illustrative and not restrictive, the scope of embodiments being indicated by the appended claims rather than the foregoing description. All changes that come within the meaning of and range of equivalency of the claims are intended to be embraced therein.

EXAMPLES

The examples set forth herein below are illustrative of different compositions and conditions that can be used in practicing the present embodiments. All proportions are by weight unless otherwise indicated. It will be apparent, however, that the present embodiments can be practiced with many types of compositions and can have many different uses in accordance with the disclosure above and as pointed out hereinafter.

Example 1

Batch Mode

To a 500 mL flask fitted with mechanical stirrer, argon inlet and reflux condenser is charged palladium(II)acetate (0.314 g, 2 mol %), CYTOP-216 (0.303 g, 2 mol %) and 45 mL of anhydrous toluene. The solution is stirred for 1 hour to allow for dissolution of palladium acetate. Then sequentially, 4-bromobiphenyl (32.8 g, 1.0 equiv), diphenylamine (26 g, 1.05 equiv), toluene (82 mL) and sodium t-pentoxide (29.1 g) are added with stirring. The reaction is heated to 90° C. over a 30 min period. A large exotherm is observed and the heating is shut off. After 1 hr 15 min the exotherm subsides and HPLC analysis confirms complete conversion of diphenylamine to N-biphenyl-diphenylamine.

Following completion of the reaction, toluene (50 mL) is added and the solution is filtered to remove insoluble materials. The solids are washed with toluene so as to have a final liqueur with a volume of 500 L. This solution is treated with Filtrol-24 (20 g) and $Al_2O_3$ (20 g) at 90° C. for 2 hours. The absorbents are filtered while the solution is hot. A second treatment with Al$_2$O$_3$ (4 g) at 90° C. is necessary to completely remove color (most likely residual palladium catalyst). The toluene solution is concentrated to 100 mL and isopropanol (150 mL) is added followed by methanol (250 mL) to complete precipitation of N-biphenyl-diphenylamine. The solid N-biphenyl-diphenylamine is filtered and washed with methanol (100 mL), air dried then finally vacuum dried (60° C./5 mmHg) overnight. The final yield of N-biphenyl-diphenylamine is 42.97 g (95.1%). HPLC, $^1$H NMR and elemental analysis confirm purity of N-biphenyl-diphenylamine at >99.5%. Ashing followed by ICP analysis does not detect any residual palladium present.

When this reaction is run in the laboratory in batch mode it is heated to the point where it self-refluxes (from exothermic self-heating) and then upon cooling the reaction is complete. In determining isothermal conditions whereby N,N-diphenyl-4-biphenylamine was produced at a reasonable rate, it was found that the reaction proceeded well at 90° C. but did not proceed at all at temperatures lower than 90° C., thus indicating the reaction has an on-off point in addition to being exothermic. Three identical runs were performed at 90° C. to measure accurately the reaction conversion kinetics.

Figure 2:
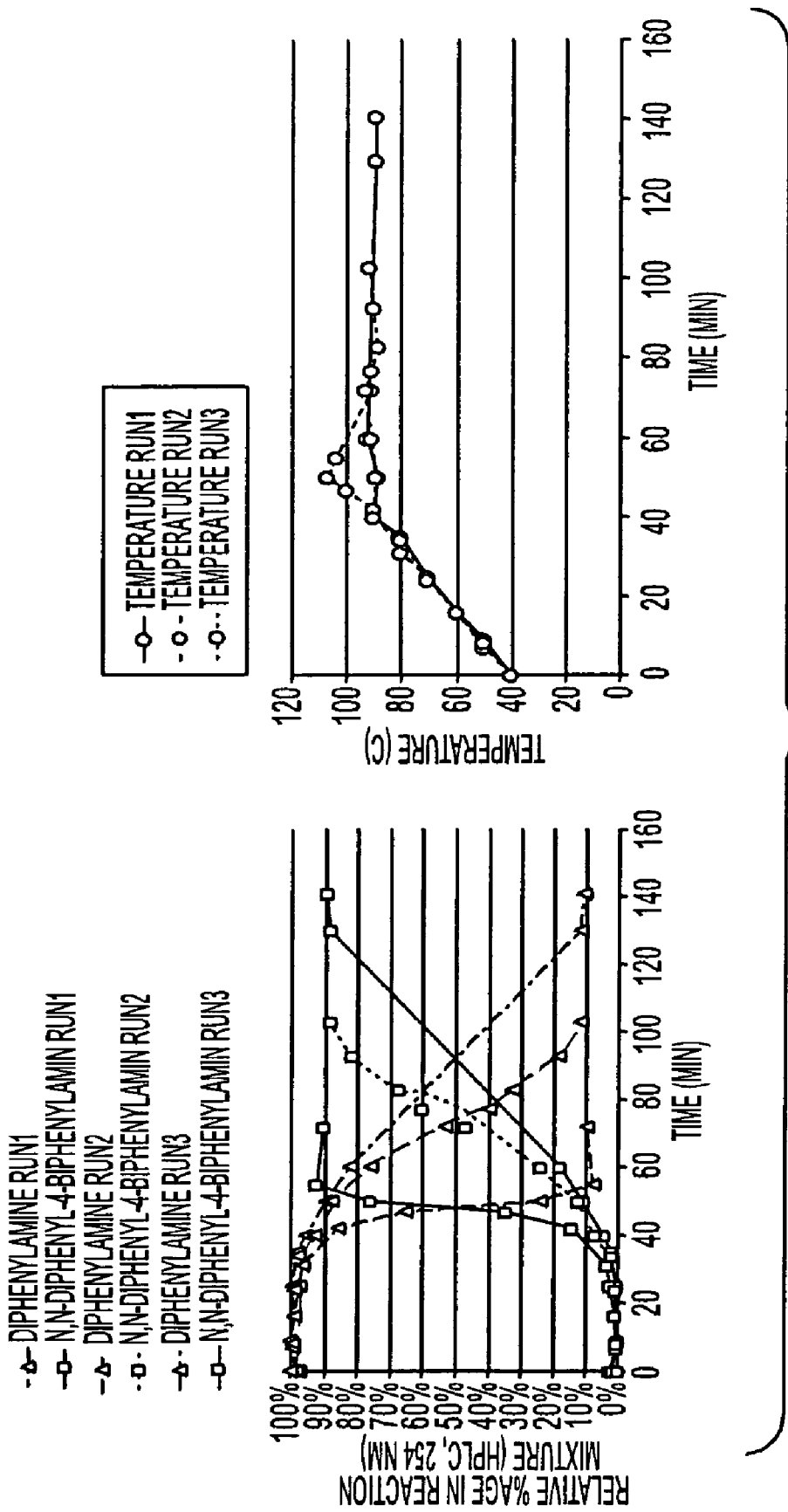
FIG. 2 is graph illustrating a conversion plot of N,N-diphenyl-4-biphenylamine reaction and comparative temperature profiles according to an embodiment of the present disclosure.

It was found that the conversion profiles for the three runs are not exactly reproducible, as seen in FIG. 2. FIG. 2 shows a conversion plot of N,N-diphenyl-4-biphenylamine reaction isothermal at 90° C. (left) and temperature profiles of same reactions (right). The additional temperatures measured during the reaction indicated that, while the heating profiles for each reaction were identical, in one of the three cases, the reaction resulted in a large exotherm and an overheating of the reaction mixture (FIG. 2). The cause of the inconsistency is unknown. Complete conversion was seen for all three reactions based on the 10% excess of diphenylamine that is present in the reaction.

Example 1a

Continuous Mode with One Solvent

With satisfactory conversion results in batch mode, the identical reaction conditions (10 mol % excess diphenylamine, Pd(OAc)$_2$/CYTOP-216 2 mol %, NaOtPen 1.2 mol equivalents, and toluene as solvent, isothermal at 90° C. were used with a continuous plug flow reactor (as shown in FIG. 1). The residence time was approximately 20 minutes and samples of approximately 10 mL were taken continuously.

Plugging of the reactor was a constant problem that required pulsing of the pressure on the input pots. However, after approximately 30 samples, the reactor plugged entirely. The plugging is presumably due to the production of insoluble sodium bromide precipitate (a known by-product of the reaction). In order to counter the plugging, several re-pipings of the plug flow reactor were tried but did not resolve the problem. Subsequently, the use of a co-solvent along with toluene was tried. The conversion of this continuous reaction was on average around 20% to produce the N,N-diphenyl-4-biphenylamine even with the plugging of the reactor.

Example 2

Batch Mode with Co-Solvent

To a 500 mL flask fitted with mechanical stirrer, argon inlet and reflux condenser is charged palladium(II)acetate (0.314 g, 2 mol %), tri-t-butylphosphine (0.310 g, 2 mol %) and 45 mL of anhydrous toluene. The solution is stirred for 1 hour to allow for dissolution of palladium acetate. Then sequentially, 4-bromobiphenyl (32.8 g, 1.0 equiv), diphenylamine (26 g, 1.05 equiv), CYPHOS IL-109 (63.5 mL), anhydrous toluene (18.5 mL) and sodium t-pentoxide (29.1 g) are added with stirring. The reaction is heated to 110° C. over a 30 minute period and the reaction was continued for 2 hours at 110° C. after which time. HPLC analysis showed a 67.9% conversion of diphenylamine to N-biphenyl-diphenylamine.

Example 2a

Continuous Mode with Co-Solvents

Figure 3:
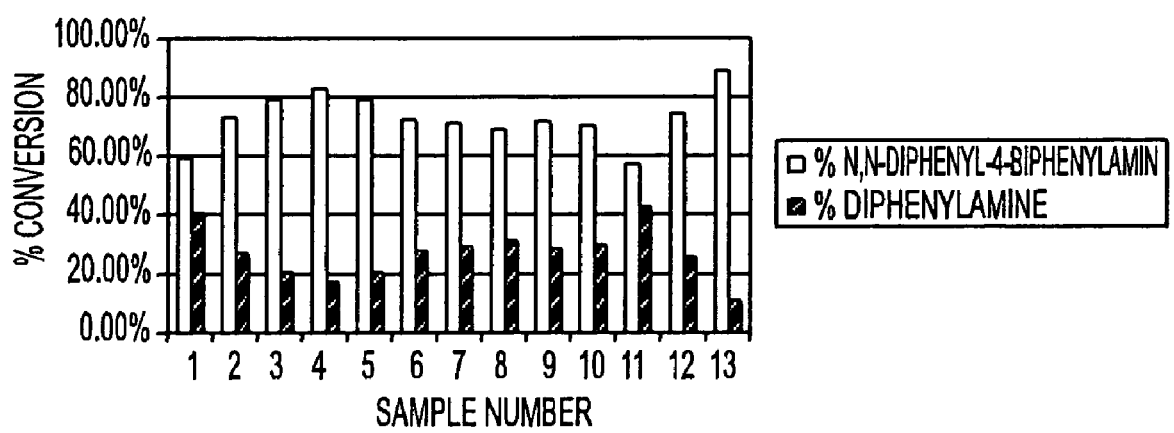
FIG. 3 is a graph illustrating conversion as a plot of sample number for a continuous reactor run according to an embodiment of the present disclosure.

With satisfactory conversion results in batch mode, the identical reaction conditions (10 mol % excess diphenylamine, Pd(OAc)$_2$/tri-t-butylphosphine 2 mol %, NaOtPen 1.2 mol equivalents, and a 50% mixture of toluene and CYPHOS IL-109 as the solvent, isothermal at 90° C. were used with a continuous plug flow reactor (as shown in FIG. 1). The desired outcome was high conversion of up to 89%, shown in FIG. 3, with no insoluble precipitates (sodium bromide solubilized) and no formation of side products.

The results demonstrate that indeed Buchwald chemistry can be run to high conversion if used in continuous mode. It is believed that the variation in conversion was related to variation in the residence time due to uneven flow characteristics; use of a pump and better flow control should allow more consistent performance. The average residence time for this reaction was 38 minutes.

Furthermore, if the residence time during the continuous process inside the reactor is considered, the processes in this example have better conversion at an equivalent time and at a lower temperature (Table 1).

TABLE 1

|  | Batch | Continuous |
|---|---|---|
| Temperature (° C.) | 110 | 90 |
| Conversion (%) | 67.9 | Up to 89 |

All the patents and applications referred to herein are hereby specifically, and totally incorporated herein by reference in their entirety in the instant specification.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

What is claimed is;

1. A method for forming N,N-diphenyl-4-aminobiphenyl, comprising reacting a first reagent with a second reagent at a temperature above 90° C., the first reagent being diphenylamine and the second reagent being 4-bromobiphenyl, the reaction taking place in a presence of a base comprising sodium t-butoxide and a palladium catalyst ligated with tri-t-butylphosphine in a continuous plug flow reactor such that N,N-diphenyl-4-aminobiphenyl is produced, and wherein the steps further comprise:

continuously reacting the 4-bromobiphenyl and the diphenylamine in a first solvent in the presence of the palladium catalyst ligated with tri-t-butylphosphine under Buchwald conditions in the continuous plug flow reactor;

adding a second solvent with sodium t-butoxide base to the 4-bromobiphenyl and the diphenylamine in the continuous plug flow reactor at a time subsequent to the addition of the first solvent to form a co-solvent system; and continuously reacting the 4-bromobiphenyl and the diphenylamine in the first solvent and the second solvent with the sodium t-butoxide base in the presence of the palladium catalyst ligated with tri-t-butylphosphine under Buchwald conditions in the continuous plug flow reactor such that N,N-diphenyl-4-aminobiphenyl is produced, and wherein all products and by-products remain solubilized;

wherein the second solvent is selected from the group consisting of a polyethylene glycol dimethyl ether, a phosphonium-based ionic liquid, and mixtures thereof.

2. The method of claim 1, wherein the first solvent is toluene.

3. The method of claim 1, wherein the base further comprises 2,4,6-trioxa-1,3,5,7-tetramethyl-8-phosphaadamantane.

4. The method of claim 1, wherein the continuous plug flow reactor comprises:

one or more input pots for receiving one or more reagents;

one or more compressed air inlets coupled to the one or more input pots for introducing compressed air into the one or more reagents;

a tubular reactor suspended in an immersion bath and in flow communication with the one or more input pots for continuously reacting the one or more reagents; and a circulation heating and refrigeration bath unit in flow communication with the immersion bath for controlling a temperature of the one or more reagents inside the tubular reactor.

5. The method of claim 4, wherein the continuous plug flow reactor further includes a product receiver unit adapted to collect and weigh the N,N-diphenyl-4-aminobiphenyl produced.

6. The method of claim 1, wherein a conversion rate of the first and second reagent to N,N-diphenyl-4-aminobiphenyl is up to 89%.

* * * * *